(12) United States Patent
Sefton

(10) Patent No.: US 6,730,308 B1
(45) Date of Patent: May 4, 2004

(54) TAZAROTENE AND ALPHA HYDROXY ACID TREATMENT FOR PSORIASIS AND/OR PHOTODAMAGE

(75) Inventor: John Sefton, Trabuco Canyon, CA (US)

(73) Assignee: Allergan, Inc., Irvine, CA (US)

( * ) Notice: Subject to any disclaimer, the term of this patent is extended or adjusted under 35 U.S.C. 154(b) by 480 days.

(21) Appl. No.: 09/264,531

(22) Filed: Mar. 8, 1999

(51) Int. Cl.⁷ .................................................. A61K 6/00
(52) U.S. Cl. ....................... 424/401; 514/168; 514/557; 514/574; 514/844; 514/847; 514/944
(58) Field of Search ................................ 514/168, 557, 514/574, 844, 846, 847, 944; 424/401

(56) References Cited

U.S. PATENT DOCUMENTS 5,091,171 A * 2/1992 Yu et al. ...................... 424/642

* cited by examiner

Primary Examiner—Thurman K. Page
Assistant Examiner—Lakshmi Channavajjala
(74) Attorney, Agent, or Firm—Robert J. Baran; Martin A. Voet; Carlos A. Fisher

(57) ABSTRACT

The present invention relates to a method of treating psoriasis and/or photo damage in humans with tazarotene in a topical composition from 0.01 to 15% by weight tazarotene, and an alpha or beta-hydroxy acid in a topical composition comprising from 1 to 25% by weight alpha or beta-hydroxy acid. Furthermore, the present invention relates to treating or preventing psoriasis and/or photo damage by topically applying to the skin of a human, tazarotene, such as a gel comprising 0.01% to 0.1%, tazarotene by weight, and an alpha hydroxy acid, such as a cream, comprising 5% to 20% alpha hydroxy acid, e.g. glycolic acid, by weight.

4 Claims, No Drawings

TAZAROTENE AND ALPHA HYDROXY ACID TREATMENT FOR PSORIASIS AND/OR PHOTODAMAGE

The present invention relates to a method of treating psoriasis and/or photo damage in humans with tazarotene in a topical composition from 0.01 to 15% by weight tazarotene, and an alpha or beta-hydroxy acid in a topical composition comprising from 1 to 25% by weight alpha or beta-hydroxy acid. Furthermore, the present invention relates to treating or preventing psoriasis and/or photo damage by topically applying to the skin of a human, tazarotene, such as a gel comprising 0.01% to 0.1%, tazarotene by weight, and an alpha hydroxy acid, such as a cream, comprising 5% to 20% alpha hydroxy acid, e.g. glycolic acid, by weight. The tazarotene topical formulation may be administered once daily in the evening and the alpha hydroxy acid formulation may be administered to the subject once or twice daily in the morning or evening or twice daily in the morning and evening. The tazarotene gel is disclosed in U.S. patent application Ser. No. 623,184, which is entitled "Stable Gel Formulation for Topical Treatment of Skin Conditions", which was filed on Mar. 28, 1996, in the name of Prakash Charu and is hereby incorporated by reference in its entirety. The alpha hydroxy acid cream may be Aqua Glycolic™ Facial Cleanser available from Allergan Herbert comprising 20%, by weight, glycolic acid in a vehicle comprising the following inactive ingredients:

Water, Ammonium Glycolate (and) Glycolic Acid, Cetyl Alcohol, Stearyl Alcohol, Sorbitol, Ammonium Laureth Sulfate, Methyl paraben and Propyl paraben.

The treatment period for psoriasis may be 12 weeks. The subjects are evaluated for lesions with a successful treatment defined as about 50% improvement or better. During the treatment period, tazarotene in combination with the glycolic acid produces significantly better results than treatment with tazarotene in combination with placebo in reducing lesions.

The present invention also relates to the use of tazarotene and an alpha or beta-hydroxy acid, e.g. glycolic acid, such as Aqua Glycolic™ Facial Cleanser, in moderating and preventing the aging changes of the exposed (sundamaged) areas of the skin, especially the face. In particular, the methods of the present invention retard the effects of photoaging of the skin due to thinning and abnormal differentiation of the epidermis, inter alia. In general, the present invention relates to methods for retarding and reversing the loss of collagen fibers, abnormal changes in elastic fibers, deterioration of small blood vessels, and formation of abnormal epithelia growths in sundamaged human skin, comprising applying topically to the surface of the skin a composition comprising effective amounts of tazarotene and an alpha hydroxy acid, e.g. glycolic acid, in an emollient vehicle in a program of maintenance therapy, whereby the skin substantially regains and maintains its firmness, turgor and elasticity during the therapy, the composition and amounts of retinoid therein, preferably, being selected so as to provide a sub-irritating dose upon application.

More specifically, the methods comprise the topical application to the surface of the skin of effective amounts of tazarotene and an alpha or beta-hydroxy acid, e.g. glycolic acid, in a program of maintenance therapy, whereby epithelial neoplasms (basal and squamous cell cancers) and pre-neuplastic growths (actinic keratoses) are substantially prevented. Also, the skin significantly regains and maintains its firmness, turgor and elasticity during the therapy. Effacement of fine wrinkles is an important clinical effect. Generally, the maintenance therapy is begun in adult life when epithelial growths and other aging changes begin to appear clinically. Pigmentary blotching and mottling are also alleviated.

The tazarotene and the alpha or beta-hydroxy acid, e.g. glycolic acid, may be applied to the skin in any non-toxic, dermatologically acceptable vehicle, preferably a non-volatile, emollient or lubricating vehicle, in an amount and at a frequency which are insufficient to cause irritation of the skin. Generally, the concentrations are low but may be suitably varied depending on the relative strength of the applied tazarotene and alpha hydroxy acid, e.g. glycolic acid.

The above method may also be used in treating acne. That is, acne may be successfully treated with tazarotene and an alpha or beta-hydroxy acid.

I claim:

1. A method for treating psoriasis and/or photodamage and/or acne in a human subject by topically applying to the psoriatic or sundamaged skin and/or acne of said subject an effective amount of tazarotene and an effective amount of an alpha hydroxy acid.

2. The method of claim 1 wherein tazarotene is applied as a 0.1% gel.

3. The method of claim 2 wherein said alpha hydroxy acid is glycolic acid and is applied as a cream comprising 20% by weight, glycolic acid.

4. The method of claim 1 wherein tazarotene is administered once daily in the evening and said alpha hydroxy acid is glycolic acid and is administered once daily in the morning or evening or twice daily in the morning and evening.

* * * * *